United States Patent [19] [11] Patent Number: 5,028,413
Bianchi et al. [45] Date of Patent: Jul. 2, 1991

[54] NOVEL FLUORIDE-CONTAINING DENTIFRICE

[75] Inventors: Alan L. Bianchi, Penfield; John T. Freiberg; Kenneth D. Konopa, both of Rochester, all of N.Y.

[73] Assignee: Bausch & Lomb Incorporated, Rochester, N.Y.

[21] Appl. No.: 497,053

[22] Filed: Mar. 21, 1990

[51] Int. Cl.$^5$ .................... A61K 7/18; A61K 7/16
[52] U.S. Cl. ............................. 424/52; 424/49
[58] Field of Search ..................... 424/49–58

[56] References Cited

U.S. PATENT DOCUMENTS

| | | | |
|---|---|---|---|
| 2,773,801 | 12/1956 | Fox | 424/49 |
| 3,228,845 | 1/1966 | Najjar | 424/49 |
| 3,257,282 | 6/1966 | Muhler | 424/52 |
| 3,892,843 | 7/1975 | Muhler et al. | 424/52 |
| 3,941,424 | 3/1976 | Balamuth et al. | 300/21 |
| 4,011,309 | 3/1977 | Lutz | 424/49 |
| 4,143,126 | 3/1979 | Gaffar | 424/49 |
| 4,165,368 | 8/1979 | Gaffar | 424/52 |
| 4,517,701 | 5/1985 | Stanford | 15/106 |
| 4,537,778 | 8/1985 | Clipper et al. | 424/53 |
| 4,684,517 | 8/1987 | Clipper et al. | 424/52 |
| 4,839,156 | 6/1989 | Ng et al. | 424/53 |
| 4,943,429 | 7/1990 | Winston et al. | 424/52 |

OTHER PUBLICATIONS

BASF Brochure, "Pluronic and Tetronic Surfactants" (Gels for Fluoridated Dentifrices, 20% concentration for Pluronic /F127 for a gel), 11 pages.

Primary Examiner—Shep K. Rose
Attorney, Agent, or Firm—Salvatore P. Pace; Craig E. Larson; Christopher E. Blank

[57] ABSTRACT

A novel aqueous-based, neutral pH gel dentifrice composition containing fluoride and optionally containing hydrated silica is provided. The dentifrice composition contains about 15% to about 25% by weight of a polyoxyethylene polyoxypropylene block copolymer gelling agent, about 5% to 15% by weight of a humectant, about 0.1% to about 4.0% by weight of a surfactant, about 0.1% to about 2% of a fluoride source, and an effective amount of a flavor ingredient and an effective amount of a buffering agent whereby the pH of the final composition is essentially neutral. The dentifrice exhibits unique rheological properties making it particularly suitable for use with electromechanical tooth brushing devices of the type having independently moving tufts.

8 Claims, No Drawings

NOVEL FLUORIDE-CONTAINING DENTIFRICE

BACKGROUND OF THE INVENTION

1. Field of the Invention

This invention relates to a novel fluoride-containing dentifrice composition. More specifically, the present invention is an aqueous-based, neutral pH gel dentifrice containing fluoride and exhibiting unique rheological properties making it particularly suitable for use with electromechanical toothbrushing or plaque removing devices.

2. Description of Background Art

The art is replete with numerous formulations and compositions of dentifrices. Dentifrices are generally formulated to provide cleaning efficacy while being pleasant tasting and beneficial to oral hygiene.

U.S. Pat. No. 2,773,801 teaches a dentifrice composition containing a water soluble condensation product of ethylene glycol and polypropylene glycol having a molecular weight of about 5,000 to about 10,000 and ethylene oxide content of about 75-90% by weight. The dentifrices disclosed therein typically have about 0.1% to 10% by weight of the condensation product. U.S. Pat. No. 4,011,309 discloses a dentifrice composition containing similar condensation products for desensitizing sensitive teeth. These compositions contain citric acid and sodium citrate and the pH of these compositions is from 5.2 to 6.2. U.S. Pat. No. 4,839,156 teaches an aqueous dental gel for oral cleaning having an acid pH and comprising 18-25% by weight of a polyoxyethylene polyoxypopylene block copolymer gelling agent, hydrogen peroxide, 15-40% by weight of a polyethylene glycol humectant, flavor and sweetening agents, and a non-ionic surfactant.

Although there are numerous prior art dentifrice formulations, none of the conventional formulations or the formulations described above provide a stable aqueous-based gel dentifrice containing a fluoride source, is suitable for oral cleaning and anti-caries applications, and exhibits unique rheological and lubricating properties necessary for use with electromechanical toothbrushing devices. Moreover, the present dentifrice composition provides for an effective delivery of fluoride to the teeth in a suitable form for use with such toothbrushing devices.

Accordingly, the present invention is a chemically and cosmetically stable dentifrice composition having (1) neutral pH, (2) effective fluoride delivery, and (3) is particularly suitable for use with electromechanical toothbrushing devices.

SUMMARY OF THE INVENTION

The present invention is a stable aqueous-based gel dentifrice composition consisting essentially of about 15% to 25% by weight of a solid flake or powder polyoxyethylene polyoxypropylene block copolymer gelling agent, about 5% to about 15% by weight of a humectant, about 0.1% to about 4.0% by weight of a surfactant, about 0.1% to about 1.2% of a fluoride source, an effective amount of a flavor ingredient, and an effective amount of a buffering agent whereby the pH of the final composition is between about 6.5 and about 7.5.

In a separate embodiment of this invention, the dentifrice composition contains an abrasive present in an amount of not more than about 10% by weight.

DETAILED DESCRIPTION OF THE INVENTION

The present invention is a novel aqueous-based gel dentifrice composition exhibiting enhanced lubricating properties having neutral pH and a high degree of fluoride delivery to the teeth. The present composition also exhibits low abrasivity. The inventive dentifrice composition contains as essential ingredients a gelling agent, a fluoride-delivery agent, a humectant, a surfactant and a flavoring ingredient.

The essential gelling agent of the present invention is a polyoxyethylene polyoxypropylene block copolymer in an amount from about 15% to about 25% by weight of the final composition. These gelling agents are known as poloxamer polyols which are non-ionic. The polyols comprise a central lipophilic molecule (polyoxypropylene moiety) surrounded by sequences of hydrophiles (oxyethylene moiety). Chemically, these polymers can be classified like those of polyethers or those of ether alcohols. Polyols are represented by the formula:

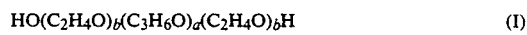

$$HO(C_2H_4O)_b(C_3H_6O)_a(C_2H_4O)_bH \qquad (I)$$

wherein a is a number which represents the moles of the lipophilic base such that it has a molecular weight of about 2800 to about 4000, and b is a number wherein $2 \times b$ equals the number of moles of the hydrophilic portion which constitutes about 70% to about 80% by weight of the copolymer. Preferably, the poloxamer polyols are of the solid type. Examples of suitable poloxamer polyols of the solid type are Pluronic® F88, F98, F108 and F127 sold by BASF Corp. of Parsippany, N.J.. These contain a lipophilic moiety of molecular weight of about 2800 to about 4000 and a hydrophilic moiety of about 70% to 80% by weight of the copolymer. The most preferred gelling agent is Pluronic® F127, with a molecular weight of about 12,500. The letters and numbers of each Pluronic® gelling agent identify and characterize the polyol. The letter indicates the physical nature of the product. (i.e. L=liquid, P=paste, F=solid). The last digit of the number multiplied by 10 represents the percentage of the part of the hydrophile in the final copolymer. The first and second digit (in the case of a three digit number) indicates the importance of the lipophilic part of the copolymer. For example, the preferred gelling agent Pluronic® F127 indicates a solid body composed of about 70% ethylene oxide and a one sequence lipophile of about 4000 molecular weight.

Generally, the solubility of these poloxamers is better in cold water than in hot water, which causes the formation of hydrogen bonding between the molecules of water and the numerous atoms of oxygen in the ether. In effect, a temperature increase is believed to provoke a rupture of the hydrogen bonds, leading to hydration of the polymer. The solubility of the poloxamers rises in an acidic solution due to the formation of oxonium ions. The incorporation of minerals (i.e. silica, $Na_3PO_4$, NaCl, etc.) or certain organic compositions (propylene glycol, glycerol or sorbitol) results in a rise in viscosity of the gel and changes the phase transition temperature by dissolving or releasing the polymer. Accordingly, the gel is thus strengthened and the viscosity is increased. Silica, however, competes with the polyol for water and care must be taken when processing the dentifrice composition to produce a final product having a suitable texture. For example, silicas may only be used up to about 10% by weight of the final product if a smooth texture is desirable.

It is believed that the polyoxypropylene lipophile on the polyol molecule interacts with the silica particles employed in a preferred embodiment, while the other end of the molecule interacts with other polyol molecules in the solution to form a particle/surfactant network. The result is a novel thixotropic gel. This unique thixotropic rheology yields a highly viscous dentifrice composition that breaks down and is free flowing when used in conjunction with brushing action. The surfactant/silica network allows for gentle cleaning of the tooth surface while lubricating the mechanical components of electromechanical toothbrushing devices as discussed below.

The humectant of the present invention can be one or more of the conventional humectants used in oral compositions such as, but not limited to, glycerin, sorbitol, and polyethylene glycols. The humectant or combination of humectants are present in amount from about 5% to about 15% by weight, preferably, from about 8% to about 13%. The preferred humectants are glycerin and sorbitol because of their gel strengthening and sweetening properties. The humectants also serve as gel strengtheners when used in combination with the gelling agent. Sorbitol, glycerin, sucrose and alkyl acetates are examples of other suitable gel strengtheners which can also be used to enhance the flavor of the dentifrice composition.

Another essential ingredient in the dentifrice of the present invention is the fluoride source. Typically, the fluoride source can be any inorganic form in which fluoride ion has combined with other elements. Typical fluoride sources include but are not limited to sodium fluoride, sodium monofluorophosphate, and stannous fluoride, with sodium fluoride being the preferred fluoride source. The fluoride source should be present in an amount to provide the highest level allowed by law. Typically, the fluoride source can be present in amounts of from about 0.1% to about 2% by weight. Currently, 0.254% by weight of sodium fluoride is the maximum amount allowed according to the United States Food and Drug Administration's dentifrice monograph and is a preferred amount of the present invention. However, the present invention can employ larger amounts of fluoride.

Yet another essential ingredient of the present invention are surfactants suitable for oral care products such as sodium lauryl sulfate, sodium lauryl sarcosinate, or other surface active agents. Typically, the surfactant is present in an amount from about 0.1% to about 4.0%. Preferred are anionic surfactants such as sodium lauryl sulfate. The use of sarcosinate compounds in the present invention is particularly advantageous in certain applications since these materials exhibit a prolonged effect in the inhibition of oral glycolysis; specifically by inhibiting the enzyme hexokinase.

It is important that the dentifrice of the present invention contain an effective amount of a flavor ingredient which will constitute from about 0.5% to about 5% by weight (including sweetening agent) of the final composition. Suitable flavoring ingredients are natural and artificial flavoring oils such as oils of spearmint, peppermint, wintergreen, menthol, sassafras, clove, eucalyptus, cinnamon, methyl salicylate, and the like. Other conventional flavoring ingredients which are well known dental and oral product components can be employed.

Included herein as part of the flavor ingredient is one or more sweetening agents which are employed as a complement to the flavoring agent. Suitable sweetening agents are generally water soluble and include but are not limited to sucrose, fructose, sodium saccharin, sodium cyclamate, xylitol, aspartame, and derivatives thereof. Typically, the concentrations of the sweetening agent will range from about 0.01% to about 1.0% by weight. Sodium saccharin is the preferred sweetening agent which is typically present in an amount from about 0.05% to about 0.2%.

Buffering agents such as phosphates, borates and the like are necessary to control the pH of the final composition. Typically, the buffering agents are present in amounts from about 0.1% to about 3% by weight in order to provide a pH in the range of about 6.5 to about 7.5. Other conventional ingredients can also be present in the inventive dentifrice composition, including but not limited to, preservatives, and coloring ingredients.

In a preferred embodiment of this invention, a suitable water-insoluble silica abrasive is included and there are a large number of such materials known in the dental art for either cleaning or polishing or both. While abrasives are an important inactive ingredient in conventional dentifrice formulations and typically comprise from 20% to 50% by weight of the total formulation, the present invention employs not more than about 10% by weight of such abrasives. Preferably, the abrasives are present in an amount from 0.1% to about 8%.

Generally, high concentrations of abrasives provide undesirable rheological properties to the dentifrice composition and have a tendency to more rapidly wear down the mechanical portions of certain electromechanical toothbrushing devices. However, certain abrasives embodied in this invention in concentrations of up to about 10% by weight have surprisingly not been found to have any significant adverse affect on such devices.

While common abrasives or abrasive systems useful in conventional dentifrices include alumina, dicalcium phosphate, chalk, insoluble sodium metaphosphate, calcium pyrophosphate and silicas, the present invention employs specifically hydrated synthetic amorphous silicas having certain chemical and particle size characteristics especially sorted for the quick release of bioavailable fluoride. The preferred abrasives for use herein are silica gels including the aerogel type silicas, the xerogel type silicas and the Sylodent ® type silicas, or combinations thereof which are commercially available from W. R. Grace & Co. The properties of aerogel and xerogel type silicas are shown in Table I.

TABLE I

| Typical Properties of Silica Aerogels and Silica Xerogels | | |
|---|---|---|
| | Xerogel | Aerogel |
| Average Partical Size (Microns) | 8 | 4 |
| Surface Area (m$^2$/gram) | 340 | 310 |
| Average Pore Diameter (Angstroms) | 150 | 200 |
| Average Pore Volume (cc/g) | 1.1 | 1.5 |
| Oil Absorption (lb/100 lb) | 70 | 300 |

Surprisingly, it has been found that certain silica gel systems are extremely useful in providing the desirable rheological properties of the present dentifrices, while maintaining the lubricating properties of the gel system.

For example, by adjusting the ratio of aerogel type silicas to other silica gel type silicas, low abrasivity, high lubricating, and effective cleaning is observed. This is particularly true when used in combination with certain electromechanical toothbrushing devices as described below.

The final dentifrice compositions of this invention will possess a pH of about 6.5 to about 7.5 and a viscosity of about 400,000 cps to about 5,000,000 cps. When silica abrasives are employed, the viscosity is generally from about 3,000,000 cps to about 5,000,000 cps. The water content of the final composition will constitute about 40% to about 70% by weight of the final dentifrice. It is preferred that the water employed be purified water to minimize mineral or bacterial contamination.

The dentifrice of the present invention may be prepared generally in accordance with U.S. Pat. Nos. 4,011,309 and 4,839,156 which are incorporated herein by reference. However, in a preferred embodiment of the present invention, the compositions are prepared according to the following procedure. The buffering agents along with the fluoride source and sweetening agents are added to water in a suitable vessel at about 19° to about 24° C. Next, the humectants/gel strengtheners are added at about 35° to about 40° C. The mixture is brought under vacuum and the silica, if desired, is added and mixed under vacuum. Mixing is continued until the silica is completely hydrated to obtain a homogeneous slurry. The gelling agent is added under vacuum along with the surfactant. The temperature of the mixture is then brought to between about 70° to about 75° C. to facilitate dissolution of the gelling agent. When the slurry is free of lumps and air, it is cooled to between about 50° to about 55° C. The flavor ingredients are then added under vacuum. A very rigid, homogeneous, stable gel dentifrice is obtained. The final product may be packaged in a suitable container such as a laminated plastic tube compatible with both the fluoride source and the flavor ingredient.

While the present dentifrice compositions are useful with conventional manual toothbrushes, they are particularly useful in combination with electromechanical toothbrushing or plaque removing devices having independently moving tufts or groups of tufts. For example, devices which employ individually moving tufts are disclosed in U.S. Pat. Nos. 4,156,620, 4,827,550 and 4,845,795. It has been found that conventional dentifrices promote wear of the brushhead gears and/or other mechanically moving components as well as the tufts of such devices. Further, use of many conventional dentifrices in combination with such devices often causes binding of the mechanical components resulting in the stoppage of the brushing motion.

Conversely, the present compositions promote mechanical movement by actively enhancing the speed or movement of the brushing motion by lubricating the movement of the brushhead mechanical components. The lubricating properties of the present invention also extends the life of the mechanical components and the tufts. Further, the present compositions are effective at removing debris and residual stain from tooth surfaces when used in combination with electromechanical toothbrushing devices although the abrasivity of the compositions are low when compared to conventional dentifrices. In the preferred embodiment, the silicas provide abrasivity to facilitate the polishing and cleaning of the tooth surfaces and the removal of plaque.

The present dentifrice is also formulated to promote dissolution and foaming in the oral cavity upon brushing and is specifically designed to promote oral hygiene in an ethical fashion by delivering fluoride to the enamel surface of teeth. For example, the present compositions have been shown to provide therapeutically effective levels of bioavailable fluoride to teeth, inhibiting demineralization and enhancing remineralization of dental enamel.

Further, the preferred embodiment herein containing certain hydrated silicas also exhibits an unexpectedly high degree of stability. For example, three months of accelerated temperature stability tests have indicated that the dentifrice compositions containing various levels of silica abrasive deliver over 95% of the available fluoride and the fluoride is substantially bioavailable. The pH of the composition remains neutral over this period. The hydrated silicas in combination with the gelling agents have also produced other stabilizing effects on the composition. For example, the melting temperature range of the compositions has narrowed significantly and the solidification temperature range has expanded the rheological properties of the final composition.

The following examples are provided to illustrate embodiments of the present invention. The compositions were prepared in accordance with the preferred method as described above.

EXAMPLE 1

A dentifrice was prepared according to the following composition and procedure:

| Composition of Example 1 | |
|---|---|
| Ingredients | Weight % |
| Deionized H$_2$O | 54.5 |
| Pluronic ® F127 | 22.0 |
| Sorbitol (70%) | 11.0 |
| Hydrated Silica (Syloden® silica gel) | 7.5 |
| Glycerin | 2.0 |
| Flavor | 1.2 |
| Sodium Phosphate dibasic | 0.6 |
| Sodium Benzoate | 0.08 |
| Sodium Fluoride | 0.24 |
| Sodium Phosphate monobasic | 0.15 |
| Sodium Lauryl Sulfate | 0.1 |
| Sodium Saccharin | 0.08 |
| Color ingredient | 0.03 |

A predetermined amount of deionized water was added to a suitable vessel and heated to about 22° C. and mixed together with the sodium phosphates, sodium fluoride and sodium saccharin. The mixture was heated to about 36° C. and sorbitol and glycerin were added. The mixture was then brought under vacuum and the silica was added and mixed under vacuum at high speed for about 15 minutes. The Pluronic ® F127 and sodium lauryl sulfate were added under vacuum. The mixture was then brought to about 74° C. and mixed at low speed for approximately 1 hour. A color ingredient was then added to the vessel and the mixture was cooled to about 52° C. with slow speed mixing. The flavor ingredient was added under vacuum at about 52° C. A very rigid, homogeneous, stable, ringing gel dentifrice was obtained having excellent fluoride stability.

EXAMPLE 2

Example 1 was repeated except that 7.5% aerogel silica was substituted for all the Sylodent ® silica. The resulting product was also a very rigid, homogeneous, stable, ringing gel dentifrice, having excellent fluoride stability.

EXAMPLE 3

Example 2 was repeated except that 2.5% Sylodent ® silica was substituted for 2.5% of the aerogel silica so that the final silica system was 5.0% aerogel silica and 2.5% Sylodent ® silica. The resulting product was also a very rigid homogeneous, stable, ringing gel dentifrice, having excellent fluoride stability.

EXAMPLE 4

Example 1 was repeated except that the silica was removed and replaced with water. The sodium lauryl sulfate was also increased from 0.1% to 0.5%. and the flavor level was reduced from 1.2% to 0.7% due to the absence of silica in the final composition. The resulting product was a crystal clear rigid homogeneous, stable, ringing gel dentifrice having excellent fluoride stability.

Examples 1-4 were tested for their effect on electromechanical toothbrushing devices using an electromechanical device as described above and commercially available under the trademark INTERPLAK ® home plaque removal instrument from Bausch & Lomb Oral Care Division, Inc. of Tucker, Ga. A commercially available market leading tartar control dentifrice was used as a control. The test investigated the effect of the inventive dentifrice on the useful life and operation of the device. Accordingly, the device was placed in a specially designed test bed and connected to a continuous power source. The test bed was filled with a 50:50 slurry of dentifrice and water. The brush was weighted with 150 grams of force and the brush was run until failure. The results are listed in Table II.

TABLE II

| Dentifrice | Hours of Operation to Failure |
| --- | --- |
| Example 1 | 25 hours |
| Example 2 | 226 hours |
| Example 3 | 64 hours |
| Example 4 | 245 hours |
| Tartar Control Crest ®* | 1 hour |

*Available from Procter & Gamble Company, Cincinnati, Ohio

The results of this test indicate that the stable, fluoride containing dentifrice of this invention significantly prolongs and enhances the operation of the electromechanical device.

It should be understood that the scope of the subject invention is not limited to the examples set forth above, but includes equivalent embodiments, modifications and variations that fall within the scope of the attached claims.

What is claimed is:

1. A method for cleaning teeth and delivering fluoride to said teeth comprising contacting said teeth with an electromechanical toothbrushing device of the type having independently moving tufts or groups of tufts in the presence of an effective amount of a dentifrice composition which enhances the operation of said device while delivering bioavailable fluoride to said teeth, said composition containing not more than about 10% by weight of an abrasive and consisting essentially of about 15% to 25% by weight of a solid flake or powder polyoxyethylene polyoxypropylene block copolymer gelling agent, about 5% to about 13% by weight of a humectant, about 0.1% to about 4.0% by weight of a surfactant, and about 0.1% 1 to about 2% of a fluoride source, an effective amount of a flavor ingredient, and an effective amount of a buffering agent whereby the pH of the final composition has a pH of between about 6.5 and about 7.5 and a viscosity from about 400,000 CPS to about 5,000,000 CPS.

2. The method of claim 1 wherein said flavor ingredient is present in an amount from about 0.5% to about 5% by weight.

3. The method of claim 2 wherein said abrasive is present in an amount from about 0.1 to about 8% by weight.

4. The method of claim 3 wherein said abrasive is selected from aerogel type silicas, xerogel type silicas, hydrated silica gels or combinations thereof.

5. The method of claim 4 wherein the viscosity is from about 3,000,000 cps to about 5,000,000 cps.

6. The method of claim 1 wherein said humectant is a combination of glycerin and sorbitol.

7. The method of claim 7 wherein said surfactant is anionic.

8. The method of claim 1 wherein said silica is selected from aerogel type silicas, xerogel type silicas, hydrated silica gels or combinations thereof.

* * * * *

UNITED STATES PATENT AND TRADEMARK OFFICE
CERTIFICATE OF CORRECTION

PATENT NO. : 5,028,413

DATED : July 2, 1991

INVENTOR(S) : Alan L. Bianchi, John T. Freiberg, Kenneth D. Konopa

It is certified that error appears in the above-identified patent and that said Letters Patent is hereby corrected as shown below:

Column 8:

In Claim 7, replace "7" with -- 6 --.

Signed and Sealed this

Tenth Day of November, 1992

Attest:

DOUGLAS B. COMER

Attesting Officer

Acting Commissioner of Patents and Trademarks